United States Patent [19]
Segermark et al.

[11] Patent Number: 5,951,466
[45] Date of Patent: Sep. 14, 1999

[54] SELF-SEATING SURGICAL ACCESS DEVICE AND METHOD OF GAINING SURGICAL ACCESS TO A BODY CAVITY

[75] Inventors: James Segermark, Gem Lake; Chris Herman, White Bear Lake, both of Minn.

[73] Assignee: ViaMedics, LLC, White Bear Lake, Minn.

[21] Appl. No.: 09/059,693

[22] Filed: Apr. 13, 1998

[51] Int. Cl.$^6$ ..................................................... A61B 17/00
[52] U.S. Cl. ........................... 600/225; 600/219; 600/233
[58] Field of Search ................................... 600/201, 204, 600/219, 225, 231, 233, 235, 239, 243, 114; 606/130

[56] References Cited

U.S. PATENT DOCUMENTS

| | | |
|---|---|---|
| 475,975 | 5/1892 | Clough .................................. 600/233 X |
| 1,157,202 | 10/1915 | Bates et al. . |
| 2,812,758 | 11/1957 | Blumenschein . |
| 3,016,899 | 1/1962 | Stenvall .............................. 606/130 X |
| 3,017,887 | 1/1962 | Heyer . |
| 3,021,842 | 2/1962 | Flood . |
| 3,656,485 | 4/1972 | Robertson . |
| 3,807,393 | 4/1974 | McDonald . |
| 3,863,639 | 2/1975 | Kleaveland . |
| 3,893,454 | 7/1975 | Hagelin . |
| 4,765,311 | 8/1988 | Kulik et al. . |
| 4,971,037 | 11/1990 | Pelta . |
| 4,998,938 | 3/1991 | Ghajar et al. ........................... 606/130 |
| 5,125,396 | 6/1992 | Ray . |
| 5,201,742 | 4/1993 | Hasson . |
| 5,375,588 | 12/1994 | Yoon . |
| 5,391,156 | 2/1995 | Hildwein et al. . |
| 5,425,357 | 6/1995 | Moll et al. . |
| 5,460,170 | 10/1995 | Hammerslag . |
| 5,505,690 | 4/1996 | Patton et al. ........................ 600/235 X |
| 5,522,791 | 6/1996 | Leyva . |
| 5,540,648 | 7/1996 | Yoon . |
| 5,613,937 | 3/1997 | Garrison . |
| 5,658,272 | 8/1997 | Hasson . |
| 5,688,223 | 11/1997 | Rosendahl . |

FOREIGN PATENT DOCUMENTS

| | | |
|---|---|---|
| 0 792 620 | 9/1997 | European Pat. Off. . |
| 40 28 651 | 3/1992 | Germany . |
| WO 96 02195 | 2/1996 | WIPO . |
| WO 98 12960 | 4/1998 | WIPO . |

OTHER PUBLICATIONS

Promotional literature for CardioThoracic Systems, published on the Internet at least as early as Feb. 14, 1998.

*Primary Examiner*—Jeffrey A. Smith
*Attorney, Agent, or Firm*—Fredrikson & Byron, PA

[57] ABSTRACT

A surgical access device (10 or 10') includes a frame defining an access port and a pair of flanges are carried on the lower surface of the frame. The flanges are pivotable between an insertion position, where their leading edges are optimally placed adjacent one another to assist in inserting the device in an incision, and a retracting position, where both flanges optimally urge upwardly against the internal surface of the patient's tissue to seat the access port. A method of the invention involves making an incision at least as long as the leading edge of such a device and inserting the leading edge of the device into the incision. The flanges are moved laterally away from one another to expand the opening in the tissue and center the access port laterally within the opening.

22 Claims, 16 Drawing Sheets

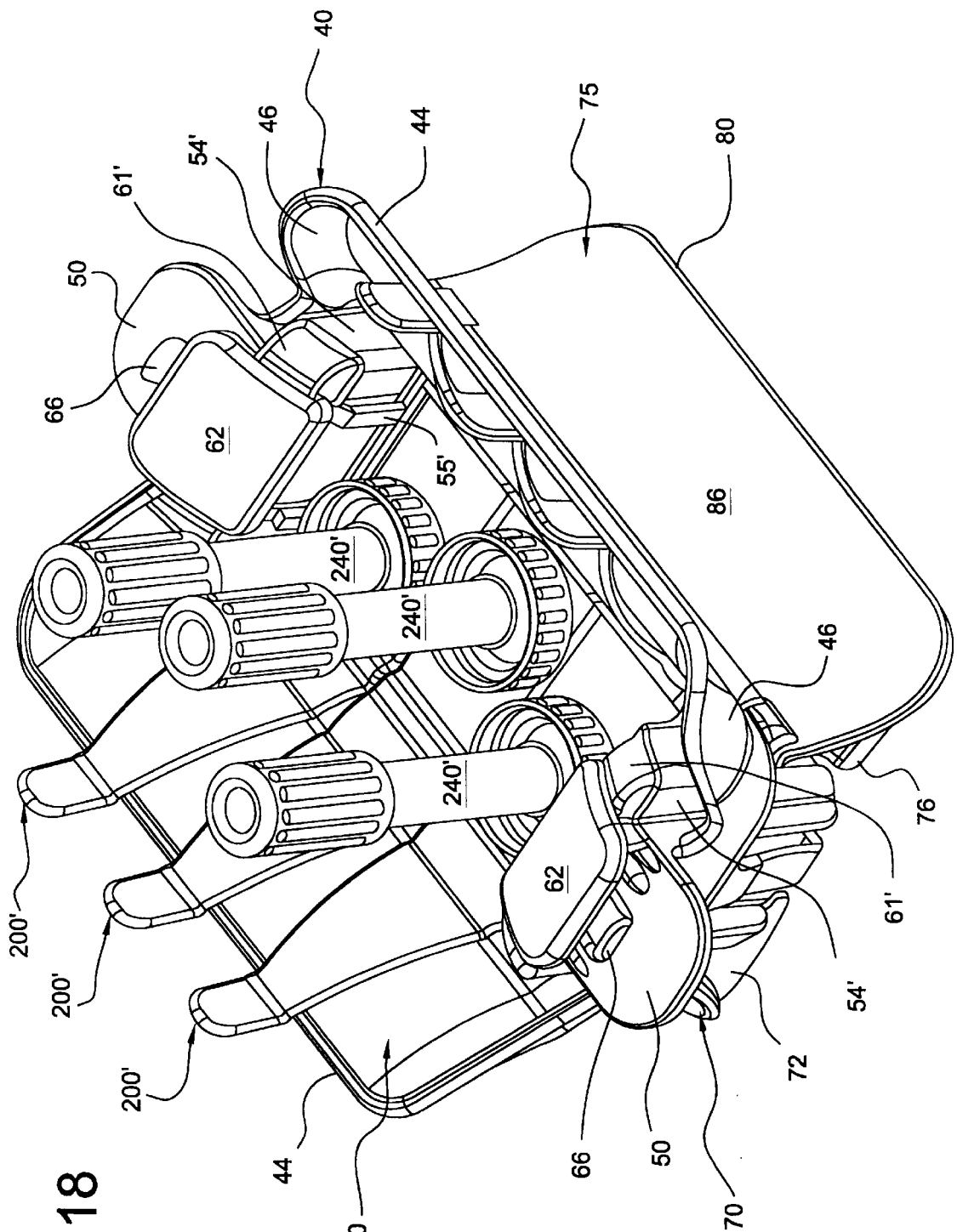

SELF-SEATING SURGICAL ACCESS DEVICE AND METHOD OF GAINING SURGICAL ACCESS TO A BODY CAVITY

FIELD OF THE INVENTION

The present invention provides an improved surgical access device of the type which is used to gain access to an internal cavity of a patient's body. A preferred embodiment of the invention is useful both as an access port and as a tissue retractor.

BACKGROUND OF THE INVENTION

Surgeons frequently need to gain access to patients' body cavities to perform various procedures. One way to gain access to such a cavity is to perform invasive surgery where the cavity is opened fairly widely from the exterior to allow the surgeon ready access to the interior of the cavity. For example, in most traditional heart surgery, the patient's sternum is split and the overlying tissue is cut back to allow the surgeon to place both hands inside the chest cavity.

Increasingly, however, less invasive techniques are being employed to permit access to body cavities. For example, endoscopic examinations are being used to explore body cavities without having to directly visually inspect them. Gall bladder surgery is also being done increasingly by gaining access to the abdominal cavity through smaller access ports through the abdominal wall rather than using more invasive approaches. (See, for example, U.S. Pat. No. 5,375,588, issued to Yoon, the teachings of which are incorporated herein by reference.)

Increasingly, surgeons are gaining access to the thoracic cavity by passing surgical instruments into the cavity through the intercostal spaces between a patient's ribs. For example, U.S. Pat. No. 5,613,937 (Garrison et al., the teachings of which are incorporated herein by reference) suggests a method of conducting closed-chest heart surgery by passing surgical implements through a number of ports positioned in the intercostal spaces. This patent shows one access cannula which provides an oblong opening which allows a surgeon to pass a replacement valve into the thoracic cavity for placement in the patient's heart.

A wide variety of surgical retractors are also known in the art. Most surgical retractors are intended to allow a surgeon to forcibly urge tissue out of the way to enable unfettered access to the underlying anatomical structures. For example, U.S. Pat. No. 4,765,311 (Kulik et al., the teachings of which are incorporated herein by reference), shows a "wound retractor" which comprises a split tube. Each of the two tube halves are carried on holders which can be moved apart from one another to retract the tissue and provide access to the abdominal cavity. U.S. Pat. No. 1,157,202 (Bates) teaches a retractor which is used to retract the sides of an incision in the abdominal wall. This retractor includes four separate retractile elements which are arranged about an oval frame. The tissue can be pulled apart to expand the size of the opening of the incision by pulling the retractile elements away from one another.

U.S. Pat. No. 5,125,396 (Ray, the teachings of which are incorporated herein by reference), suggests a surgical retractor which comprises two separate arcuate blades. Each of these arcuate blades is carried by a separate ring. By turning these two rings with respect to one another, one can move the blades with respect to one another to open a generally cylindrical passageway through the patient's tissue.

SUMMARY OF THE INVENTION

The present invention contemplates both a surgical access device and a method of gaining surgical access to a body cavity. In accordance with one embodiment, a surgical access device of the invention has a frame defining an access port and this frame has a lower surface. A first flange having an elongate leading edge is carried on the lower surface of the frame adjacent a first side of the access port. The first flange is pivotable between an insertion position and at least one retracting position. A second flange, which also has an elongate leading edge, is carried on the lower surface of the frame adjacent a second side of the access port, the first and second sides of the access port being opposite one another. Like the first flange, this second flange is being pivotable between an insertion position and at least one retracting position. Each of the first and second flanges are shaped so that when they are both in their insertion position, their leading edges are positioned immediately adjacent one another and together define an elongate, generally linear leading edge of the device which can be inserted into a single, elongate incision. This leading edge of the device is positioned below the access port. In a preferred arrangement, the first flange is attached to the lower surface of the frame by a first hinge and the second flange is attached to the lower surface of the frame by a second hinge, with the first and second hinges being parallel to one another and extending generally longitudinally along the lower surface of the frame.

In accordance with an alternative embodiment of the invention, a surgical access device includes a frame defining an access port and this frame has a lower surface. The frame also includes a pair of laterally extending wings having a concave lower surface extending generally upwardly away from opposed first and second longitudinal sides of the access port. A first flange is carried on the lower surface of the frame adjacent the first side of the access port and is pivotable between an insertion position and at least one retracting position. A second flange is carried on the lower surface of the frame adjacent the second side of the access port and is also pivotable between an insertion position and at least one retracting position. When the first and second flanges are in their retracting positions, they are adapted to urge upwardly against an internal surface of a patient's tissue to seat the access port below the tissue's upper surface. In one preferred configuration, each of the first and second flanges has a concave outer face adapted to face the internal surface of the tissue and retain the tissue between the flange and the lower surface of the adjacent wing.

As noted above, the invention also contemplates a method of gaining surgical access to a body cavity. One such method includes providing a surgical implant comprising a frame defining an access port; a first flange carried on a lower surface of the frame and having an elongate leading edge; and a second flange carried on the lower surface of the frame and having an elongate leading edge, the second flange being adjacent a side of the access port opposite the first flange. The leading edges of the first and second flanges are desirably positioned immediately adjacent one another to together define an elongate, generally linear leading edge of the implant. The operator makes an elongate, generally linear incision through the patient's tissue, with the incision being at least as long as leading edge of the implant. The leading edge of the implant can then be inserted into the incision and a length of each of the first and second flanges can be urged through the incision. The first and second flanges can be urged laterally away from one another, thereby simultaneously expanding the opening through the patient's tissue defined by the incision and centering the access port laterally within the opening.

In one further embodiment, the method also employs a resilient membrane having an external portion. Prior to the insertion of the leading edge of the implant into the incision through the tissue, the external portion of the resilient membrane is positioned over the patient's tissue surrounding the incision site. After the flanges have been urged through the incision, and preferably after the flanges are urged laterally away from one another, the implant is withdrawn from the opening, leaving the resilient membrane in place over the patient's tissue.

BRIEF DESCRIPTION OF THE DRAWINGS

FIG. 18 is a top perspective view of the surgical access device of FIG. 13, but having three of the inserts of FIG. 17 installed thereon.

DETAILED DESCRIPTION OF THE PREFERRED EMBODIMENTS

FIGS. 1–10 illustrate one currently preferred embodiment of the present invention. This surgical access device 10 includes a frame 20 having an access port 22 which extends therethrough. This access port can take any desired shape or dimension to achieve a particular clinical objective. For example, the access port can be circular, elliptical, or square. In the illustrated embodiment, though, the access port is generally rectangular in shape, having a longitudinal length greater than its transverse width. Such a design is particularly useful when utilizing the access port in a patient's intercostal space because the distance between the ribs will effectively limit the width of the device. The dimensions of this access port will vary significantly depending on the body cavity being accessed and the reason for such access. If one is utilizing the access port to gain access to a patient's thoracic cavity through an incision through the intercostal space, typical dimensions of the access port for an adult patient would be on the order of 2.5 inches (about 6.3 cm) long and 1.5 inches (about 3.8 cm) wide.

Figure 2:
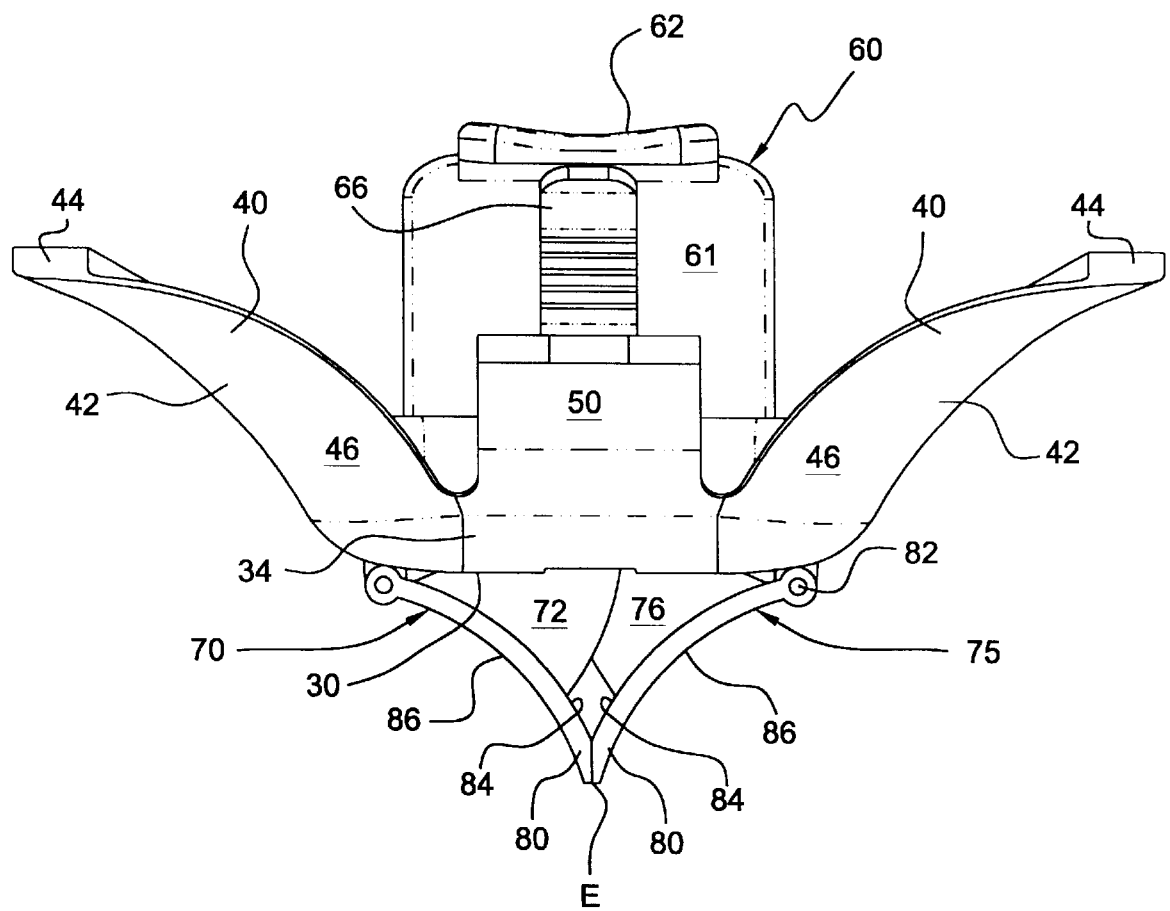
FIG. 2 is an end view of the access device of FIG. 1.
Figure 3:
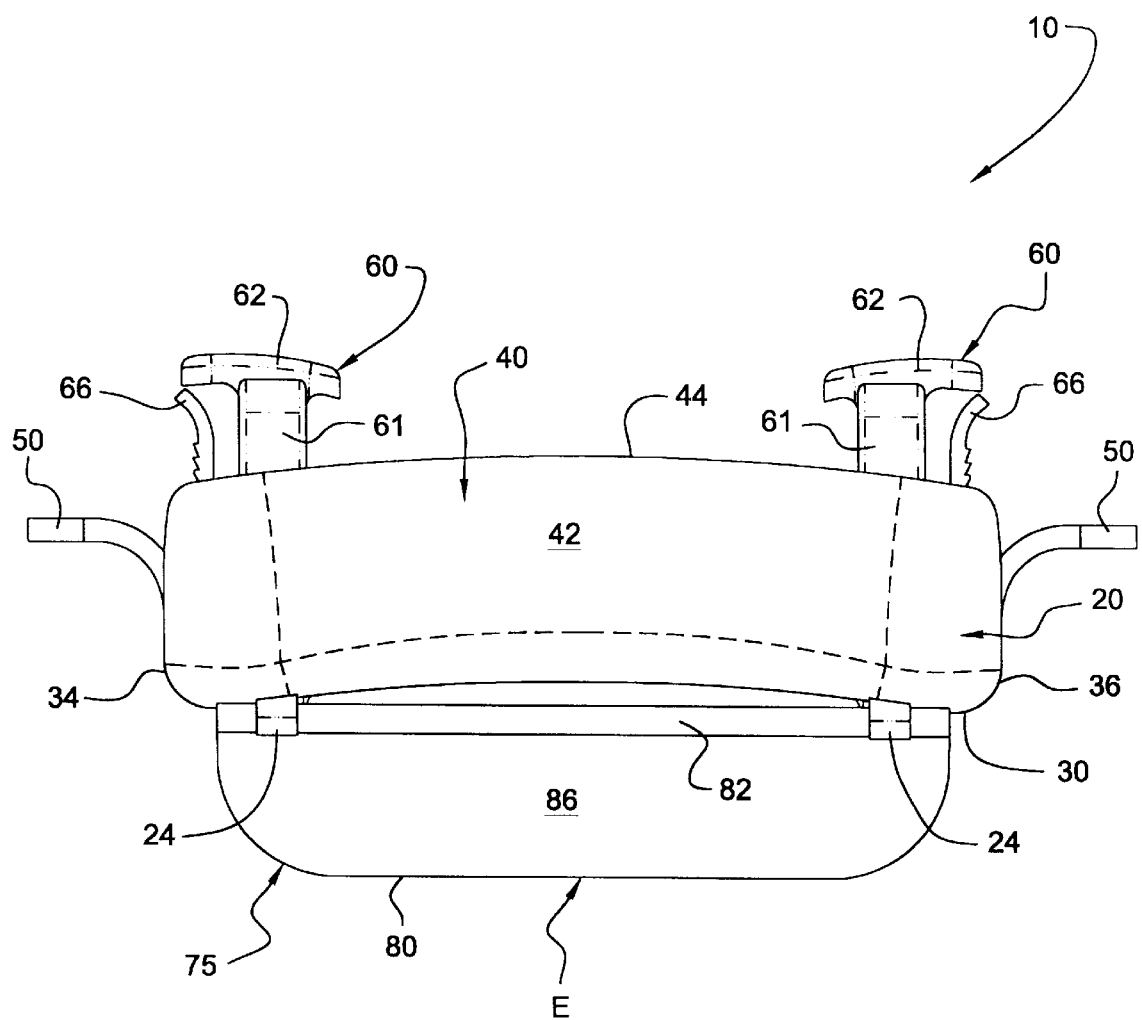
FIG. 3 is a side view of the access device of FIG. 1.
Figure 4:
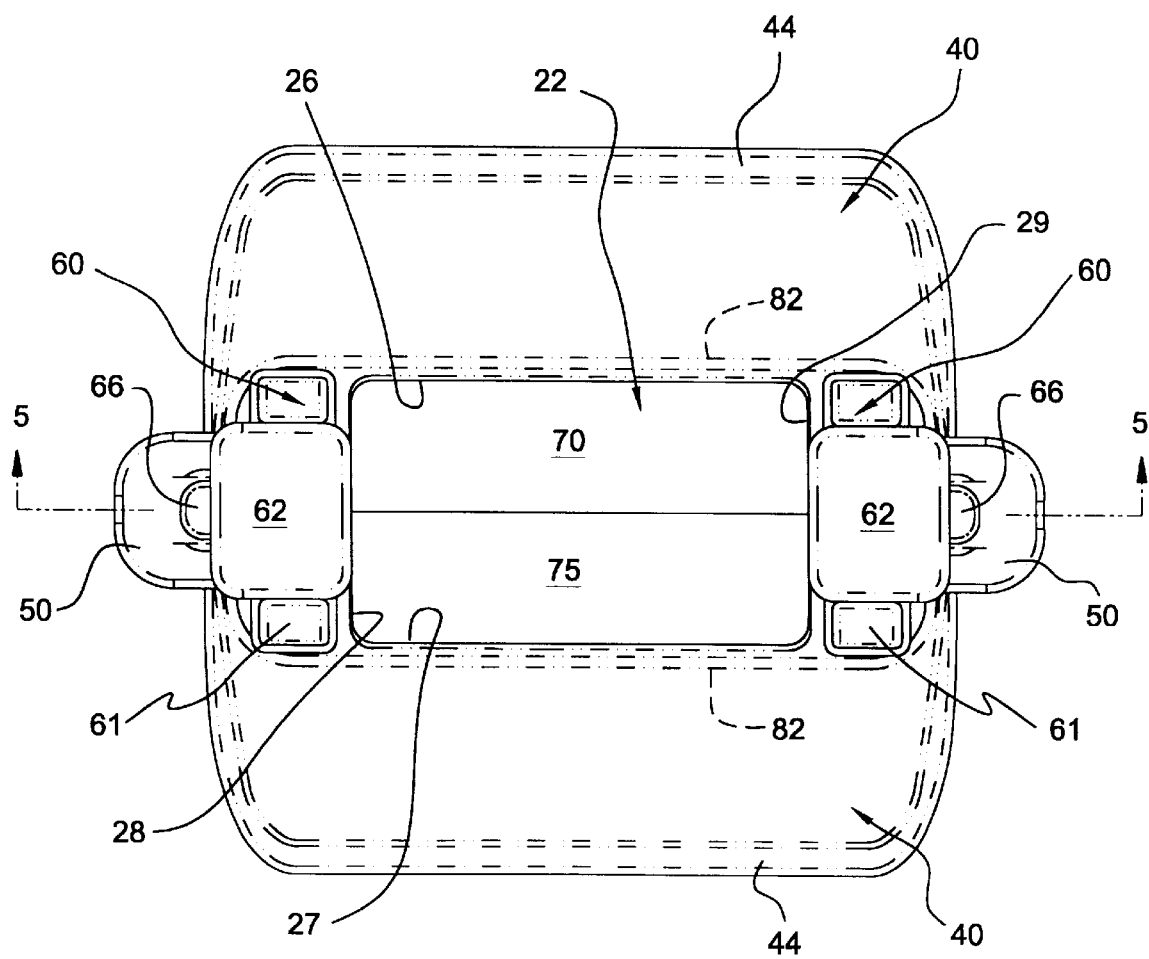
FIG. 4 is a top view of the access device of FIG. 1.
Figure 5:
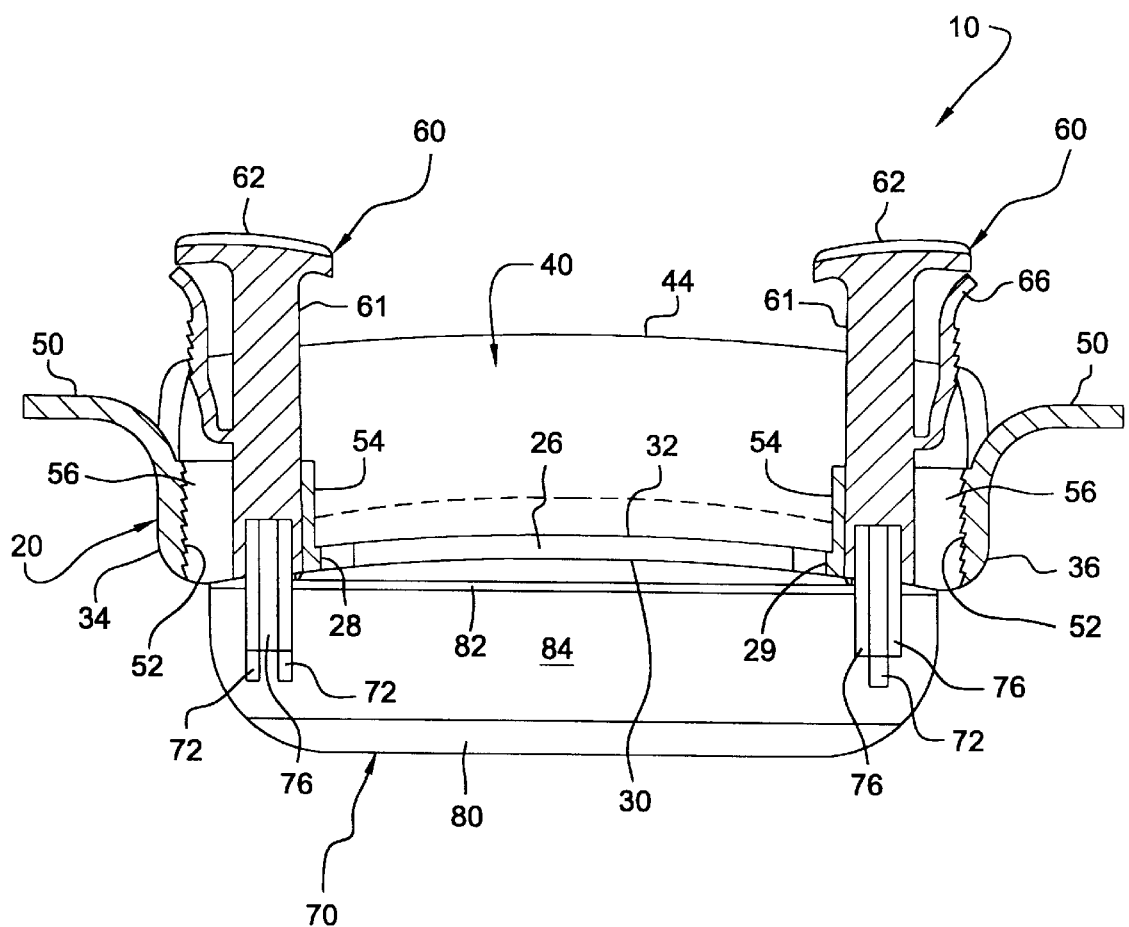
FIG. 5 is a cross sectional view taken along line 5—5 of FIG. 4.
Figure 6:
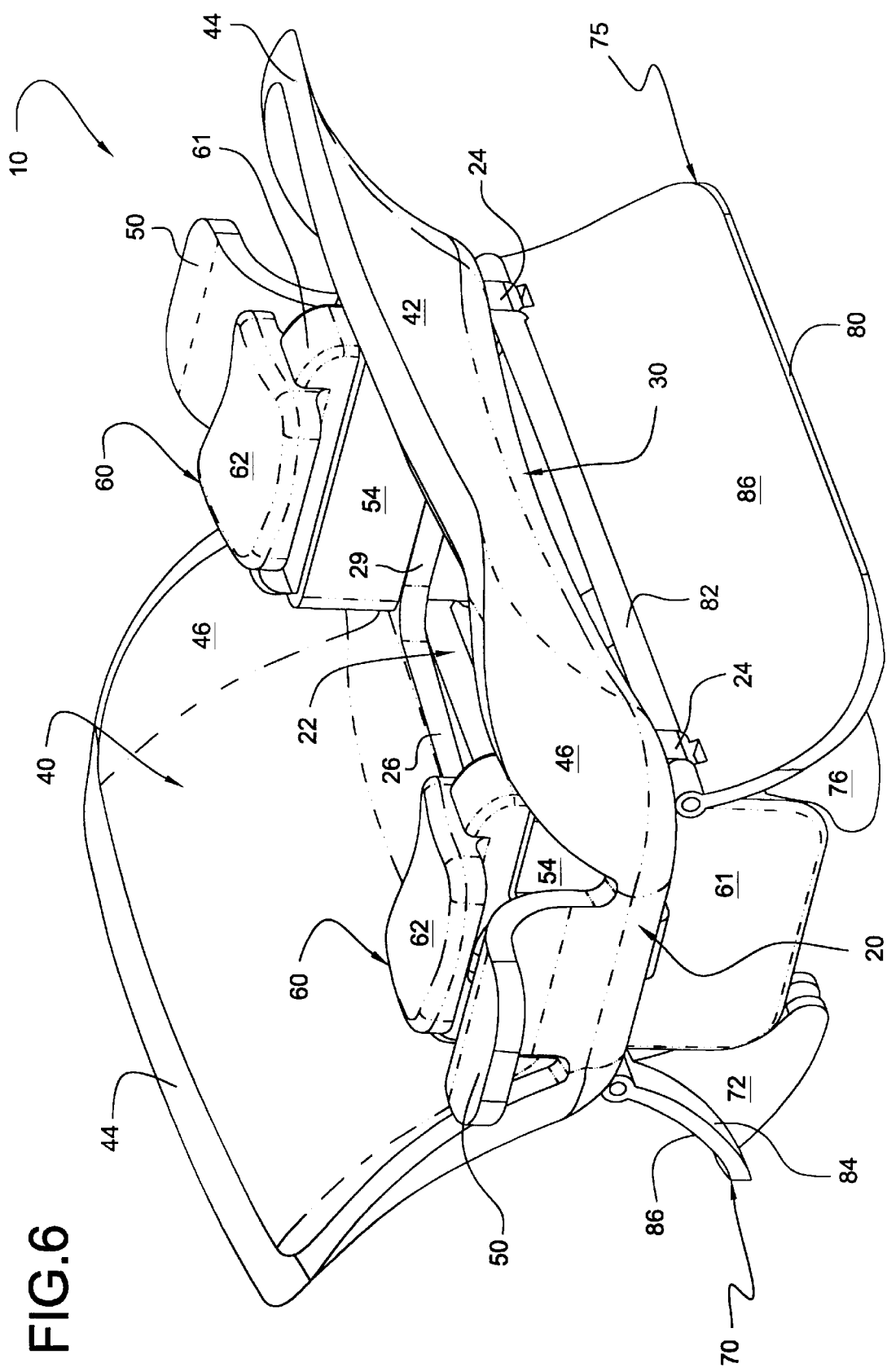
FIG. 6 is a top perspective view of the access device of FIG. 1, but wherein the flanges are in a retraction position.

The frame 20 has a lower surface 30 and an upper surface 32 (best seen in FIGS. 4 and 5). In one simplified embodiment, the frame is generally rectangular in shape and is substantially planar. In the embodiment shown in FIGS. 1–10, though, the frame has is curved both longitudinally and laterally. As best seen in FIG. 3, the lower surface 30 of the frame is curved in a longitudinal direction, defining a generally concave shape of that lower surface. This curvature may be optimized so that it will generally track the anticipated degree of curvature of the patient's chest when the surgical access port 10 is properly seated in the intercostal space (as described more fully below).

The frame 20 can be more radically curved in a transverse direction. As best seen in FIG. 2, the frame has a pair of wings, with one wing 40 extending upwardly at an angle from either side of a central portion of the frame. Desirably, the access port 22 is defined entirely within boundaries of this central portion. In the illustrated embodiment (as best seen in FIGS. 1 and 4), the access port extends right up to the lateral margins of the central portion so that each wing extends at an angle upwardly from a position adjacent one of the longitudinal sides 26, 27 of the access port.

Each of the wings includes a generally concave outer surface 42. As shown in FIG. 2, the outer surface of the wing curves relatively gradually upwardly from the lower surface 30 of the frame to the upper edge 44 of the wing. As will be explained more fully below, the wings are well suited to keep outer layers of the tissue in which the incision is made away from the access port 22. Desirably, this curvature is generally parabolic, with a steeper upward incline adjacent the central portion of the frame than adjacent the upper edge 44 of the wing. As a matter of fact, the lower surface 42 of the wing 40 may be very nearly vertical immediately adjacent the central portion of the frame while the lower surface is virtually horizontal adjacent the upper edge 44. This will make it easier for the access port 22 to be seated below the upper surface of the tissue in which the incision is made without unduly restricting the physician's ability to freely manipulate tools through the access port.

Figure 1:
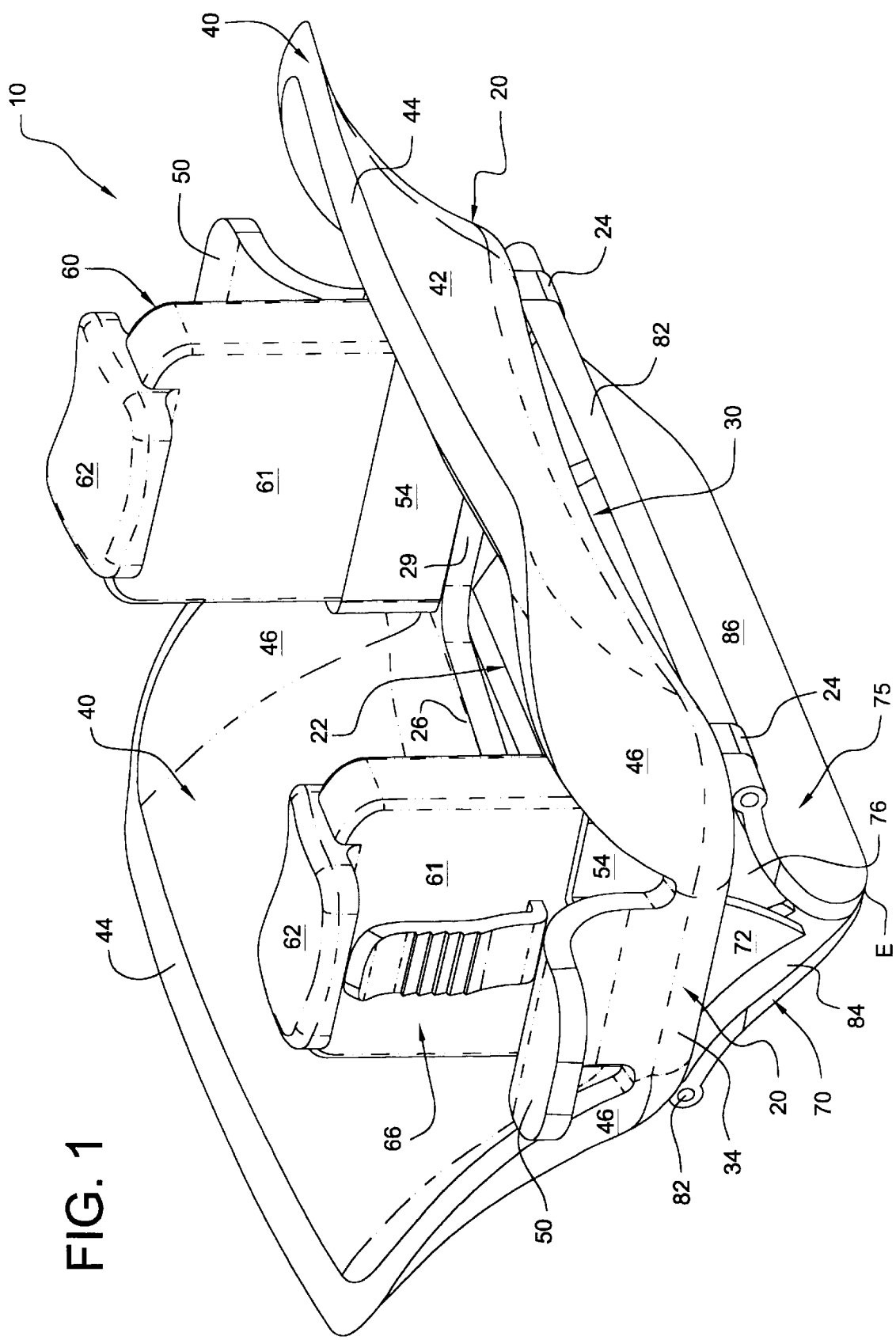
FIG. 1 is a top perspective view of a surgical access device in accordance with one embodiment of the present invention.

As best seen in FIG. 1, each side of the wing 40 is provided with a curved side 46. The curved side tapers transversely from its lower end (adjacent the central portion of the frame) up to the upper edge 44 of the wing. While these sides 46 can be omitted, the sides do help provide the device 10 with a relatively smooth, atraumatic surface to minimize any unnecessary trauma to the tissue at the surgical site. Care should be taken to minimize interference with the physician's access to the body cavity through the access port, though.

Each of the first and second ends (34 and 36, respectively) of the frame 20 includes a manually graspable tab 50. The manually graspable tab desirably extends longitudinally outwardly from the end of the frame with which it is associated. The tab 50 should extend far enough beyond the rest of the frame to permit an operator to place a finger under the manually graspable tab to deploy the flanges 70, 75 in a manner described below. Each of the manually graspable tabs has a base 54 that has an actuator channel 56 extending downwardly therethrough. This actuator channel is sized to slidably receive an actuator 60 therein. While the operation of the actuator will be discussed in more detail later, it is worth noting that the manually graspable tab 50 and the actuator 60 both may include a mechanism serving as a ratchet fitting to limit upward movement of the actuator within the actuator channel 56. In the embodiment illustrated in FIGS. 1–10, this ratchet fitting comprises a series of teeth provided on an inner surface 52 of the actuator channel 56 (best seen in FIGS. 5 and 10), with these teeth engaging mating teeth on a portion of the actuator 60 to hold the actuator in a lower position.

As noted above, a pair of flanges extend downwardly from the lower surface 30 of the frame 20. More specifically, a first flange 70 is carried on the lower surface 30 of the frame adjacent the first longitudinal side 26 of the access port while a second flange 75 is carried on the lower surface 30 of the frame adjacent the second longitudinal side 27 of the access port. Each of these flanges is pivotable between an insertion position (shown in FIGS. 1–5) and at least one retracting position (one of which is shown in FIGS. 6–10).

The pivotable connection between the flanges 70, 75 and the frame 20 can be achieved in any desirable fashion. In the illustrated embodiment, the upper edge of each flange defines a hinge 82. This hinge is adapted to mate with one or more hinge fittings 24 carried by the lower surface 30 of the frame. As noted above, in the illustrated embodiment the lower surface 30 of the frame is curved in a longitudinal direction. This means that the middle of the central portion of the frame is spaced above the horizontal level of the first and second ends 28, 29 of the access port. In order to ensure relatively smooth pivoting about a well-defined pivot access, the hinge 82 of each frame is desirably attached to two spaced-apart hinge fittings, with one hinge fitting 24 being positioned adjacent either end of the flange. This will permit the hinge to pivot freely without interference from the lower surface of the frame while maintaining mechanical simplicity. While these hinge fittings can take any desirable form, they may simply comprise a downwardly extending body with a pair of laterally extending hubs (not shown) which are received in mating recesses (not shown) provided on opposed faces of the hinge 82. Such snap-fit hinges are well known in the art and other alternative structures will be readily apparent to the average practitioner.

These two hinges 82 define pivot axes for their respective frames. The hinges are generally parallel to one another and they are both carried on the lower surface 30 of the frame. As a result, the two pivot axes together define a plane which is generally horizontal in the position shown in FIGS. 1–10. As explained below, the leading edge E of the surgical access device 10 is inserted into an incision in the patient's skin in a direction which is generally vertical in these same drawings. As a consequence, the plane defined by these two horizontal axes is generally perpendicular to the direction in which the leading edge E of the device is inserted into that incision.

Each of the first and second flanges 70, 75 has a leading edge 80 which extends longitudinally along the portion of the flange spaced farthest from the hinge 82. When the two flanges are in their insertion position, the leading edges 80 thereof will be positioned immediately adjacent one another. Optimally, the leading edges 80 directly abut one another.

The embodiment of FIGS. 1–10 utilizes a bevel adjacent the leading edge 80 of each flange to permit the leading edges to be positioned flush with one another. As best seen in FIG. 2, when these beveled faces of the flanges abut one another, they define a relatively narrow elongate leading edge E of the surgical access device 10. Desirably, the leading edges 80 of the two flanges 70, 75 and the leading edge E of the device 10 are generally parallel to the hinges 82 of the flanges and the respective pivot axes the hinges define.

Each of these flanges may be generally flat, planar structures. The preferred embodiment shown in FIGS. 1–10 employs curved flanges, however. In particular, each flange may have a convex inner face 84 which is oriented toward the access port 22 when the flange is in its insertion position (FIGS. 1–5). More importantly, though, the outer face 86 of each flange is generally concave. This concave outer face 86 is adapted to contact tissue into which the device 10 is inserted and to retain the tissue between the flange 70 or 75 and the lower surface of the frame 20. More particularly, when the flanges are in a retracting position (one of which is shown in FIGS. 6–10), a patient's tissue will be disposed in the space between the concave outer face 86 of each flange and the outer surface 42 of the adjacent wing 40. This will both help anchor the surgical access device 10 in place and, as explained more fully below, pull the frame 20 downwardly to better seat the device within the incision.

Some prior art retraction devices utilize curved blades. For example, U.S. Pat. Nos. 4,765,311 (Kulik et al.) and 5,125,396 (Ray), both of which are mentioned above in the background discussion, each provide a retractor with blades extending downwardly into an opening. These blades are defined as curved surfaces which are essentially arcs of an elongate tube. In the Kulik et al. and Ray devices, though, the curved blades are curved about a vertical axis, i.e., an axis which is generally perpendicular to a line tangent to the tissue in which it is being inserted and generally parallel to the direction in which the device is inserted into the incision in the patient's tissue.

The flanges of the present invention, however, are curved in a different orientation. The shape of each of the flanges 70, 75 may be described as a series of longitudinally extending lines, each of which is parallel to and spaced from a common axis. This common axis extends horizontally, i.e., it is generally parallel to the pivot axis of the flanges.

Figure 7:
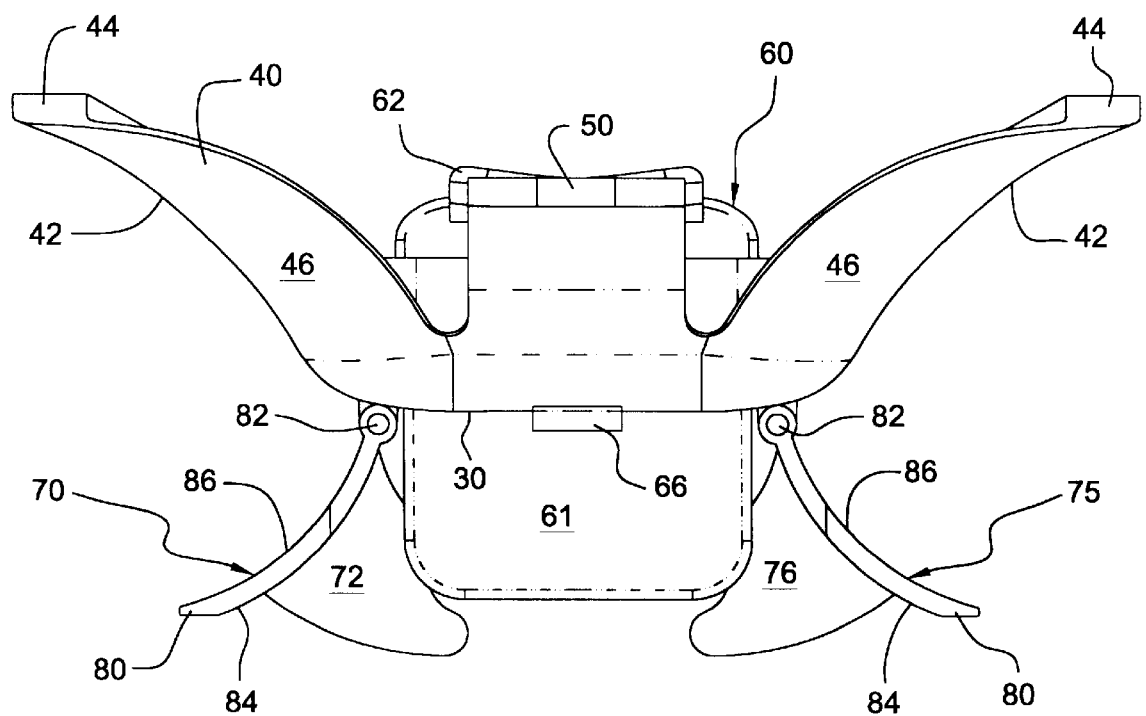
FIG. 7 is an end view of the access device of FIG. 6.
Figure 8:
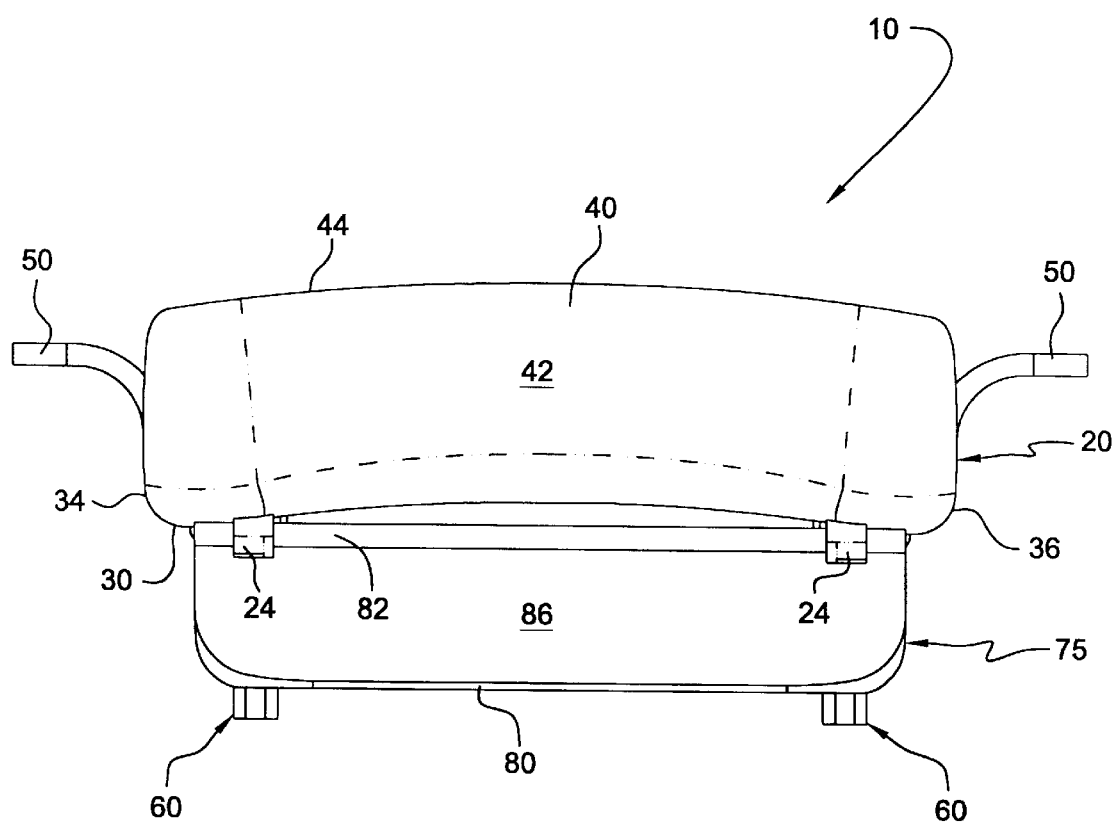
FIG. 8 is a side view of the access device of FIG. 6.
Figure 9:
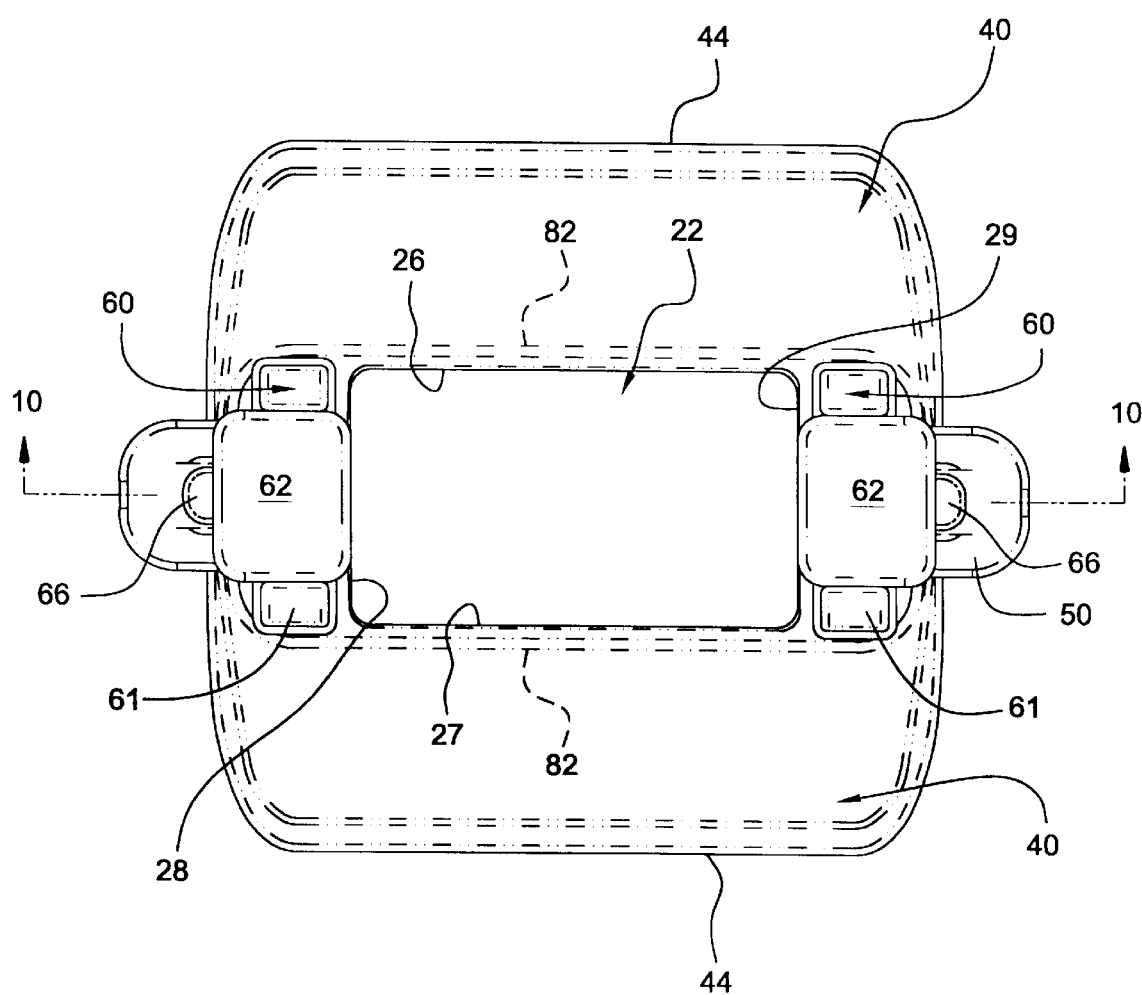
FIG. 9 is a top view of the access device of FIG. 6.

The orientation of the concave outer face 86 of the flanges with respect to the frame 20 will change as the flanges move from their insertion position to their various retracting positions. As best seen in FIG. 2, when the flanges 70, 75 are in their insertion position, the outer face 86 is concave in a direction which faces outwardly and downwardly away from the lower surface 30 of the frame. When the flanges are pivoted well away from their insertion position into one of their more distant retracting positions (e.g., as shown in FIG. 7), though, the outer face 86 of the flanges are concave in a direction oriented generally upwardly. This orientation will facilitate grasping the bottom of the tissue in which the device 10 is inserted and urging the tissue upwardly toward the adjacent wing 40 of the frame.

The flanges can be moved from their insertion position to their various retraction positions by any desired means. In its simplest form, the surgical access device 10 could simply comprise the frame 20 and the flanges 70, 75, allowing the operator to manually move the flanges apart, e.g., by pressing a finger against the inner faces 84 of the flanges. This will not give the operator very much leverage, though, and the force the operator can practically exert on the flanges with a finger may well be insufficient to retract the tissue with the flanges to seat the device 10.

In addition, if the flanges move the tissue outwardly to increase the size of the opening through the tissue, the tissue will tend to urge the flanges back toward their insertion position. The operator could either continue to hold the flanges in their retraction position or wedge something between them to maintain that position, but that is rather impractical. The surgical access device 10 desirably includes some mechanism for retaining the flanges 70, 75 in at least one retraction position to free the operator's hands and maximize the opening provided by the access port. For example, the hinges 82 may be designed to lock the flanges in at least one retraction position once the flanges are spread far enough apart. In order to permit the physician to remove the device 10 without destroying it, some mechanism for releasing the hinge should also be provided.

FIGS. 1–10 illustrate one particularly preferred embodiment which utilizes a separate actuator 60. As noted above, this actuator 60 is designed to be slidably received in an actuator channel 56 provided in the base 54 of the manually graspable tabs 50. The illustrated actuator 60 includes a body 61 with a manually engagable pad 62 provided at the top of the body. The body should be designed to fairly snuggly fit in the actuator channel 56 to ensure that it travels primarily upwardly and downwardly within the channel without too much lateral motion.

The embodiment of FIGS. 1–10 employs a body which has a smooth outer surface received in a relatively smooth actuator channel. In the alternative embodiment of FIG. 13, though, the actuator channel 54' has a pair of parallel recessed tracks 55'. The body 61' of the actuator 60' has a pair of parallel, spaced-apart rails 63' which are adapted to be slidably received within the recessed tracks 55' of the base 54'. As an operator pushes downwardly against the pad 62 at the top of the body, the rails 63' and recessed tracks 55' will help guide the actuator downwardly along a vertical path.

The actuator 60 can be adapted to directly engage the inner face 84 of each of the flanges 70, 75 to urge them out of the way. If so desired, though, a more complex cam arrangement can be utilized to enhance mechanical advantage of the actuator and improve the ability of the operator to retract tissue with the flanges 70 and 75.

In the illustrated embodiment, each flange is provided with at least two cam plates which extend inwardly from the inner face 84 of the flange. In particular, the first flange 70 has three inwardly extending cam plates 72 and the second flange 75 has three inwardly extending cam plates 76. As best seen in FIG. 5, at each end, the cam plate from one of the two flanges can be received between two adjacent cam plates from the other flange. For example, FIG. 5 shows the flange 70 having a pair of spaced-apart cam plates 72 at the left end of the flange with a single cam plate 72 at the right side of the flange. The second flange 75 (not itself visible in FIG. 5) has a single cam plate 76 on its left side and this cam plate is received between the two adjacent cam plates 72 of the first flange 70. Conversely, the right side of the second flange 75 is provided with a pair of cam plates 76 and the single cam plate 72 of the other flange 70 is received between those two cam plates. This helps guide the flanges along a predefined path and limit tortional stress on the hinges 82. To simplify manufacturing, though, one could provide just two cam plates on each flange, with one of these plates being positioned beneath each of the actuators 60.

Figure 11:
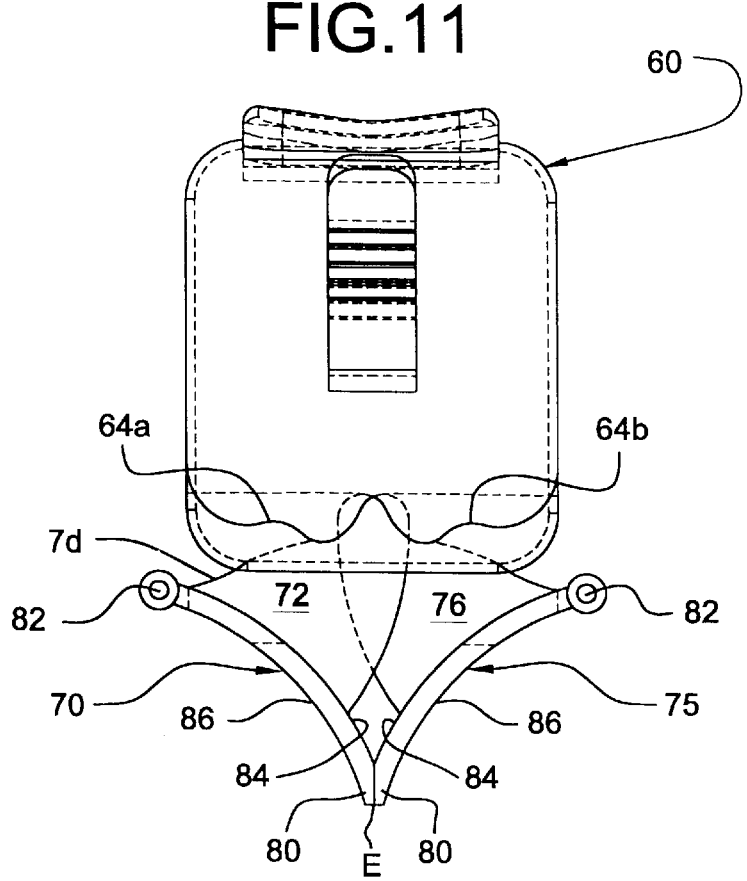
FIG. 11 is an isolational end view of a portion of the access device of FIG. 1, schematically illustrating the engagement between an actuator and the flanges when the flanges are in their insertion position.
Figure 12:
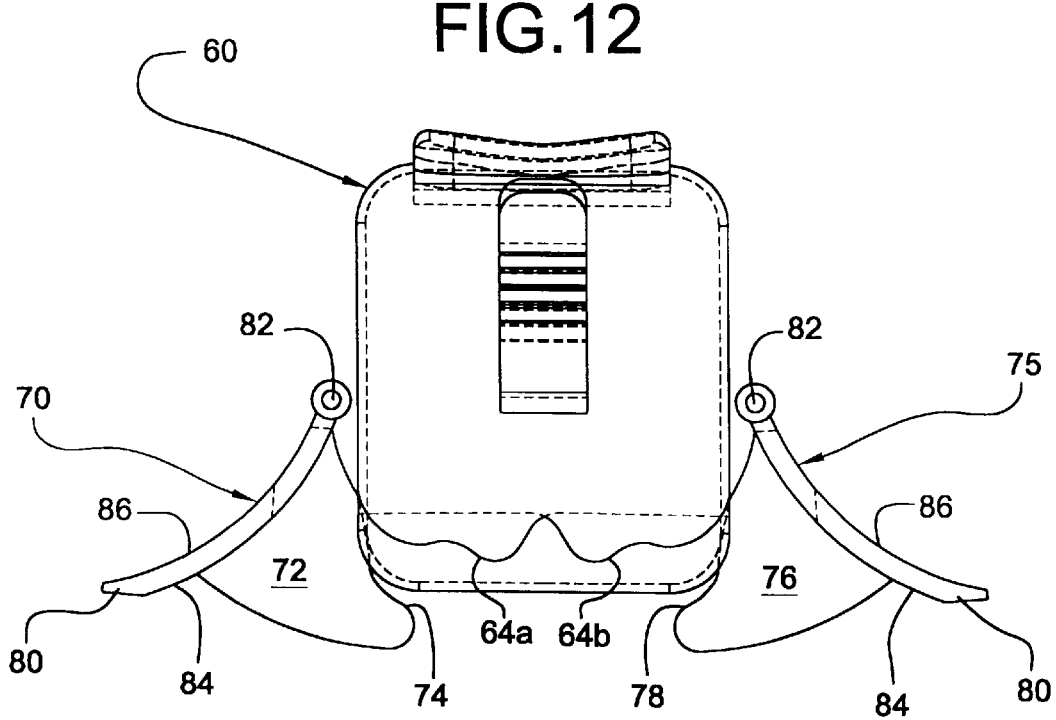
FIG. 12 is an isolational end view similar to FIG. 11, but schematically illustrating the engagement between the actuator and the flanges when the flanges are a retraction position.

FIGS. 11 and 12 are schematic drawings showing only the actuator 60 and the flanges 70, 75 in a simplified end view. FIG. 11 shows these elements with the flanges in their insertion position while FIG. 12 shows the physical relationship of these elements with the flanges in a retraction position.

The cam plates 72 of the first flange 70 have an upper cam surface 74 while the cam plates 76 of the other flange 75 have an upper cam surface 78 which is desirably the mirror image of the cam surface 74 on the other flange. The lower portion of the actuator 60 is provided with a control surface 64. In the illustrated embodiment, the control surface is actually divided into two effective surfaces 64a and 64b. The control surface 64a is adapted to engage the upper surface 74 of the cam plate 72 while the other control surface 64b is adapted to engage the upper surface 78 of the cam plate 76. As noted above in connection with FIGS. 5 and 10, the cam plates 72 and 76 are positioned adjacent to one another. As a consequence, these control surfaces 64a and 64b would be positioned side-by-side one another, but can overlap one another laterally if deemed necessary.

The specific shapes of the control surfaces 64 of the actuator 60 and the upper surfaces of the cam plates can be varied as desired. The illustrated design is useful for maximizing the initial mechanical advantage when the operator first pushes downwardly on the actuators to help spread the tissue apart. Once the flanges have been moved away from their insertion position (FIG. 11), the surfaces of the cam plates and the actuator are shaped to maximize the motion of the flanges for the limited vertical travel of the actuator. A wide variety of different cam services can be employed to achieve the specific design objectives of a given application, however.

Figure 10:
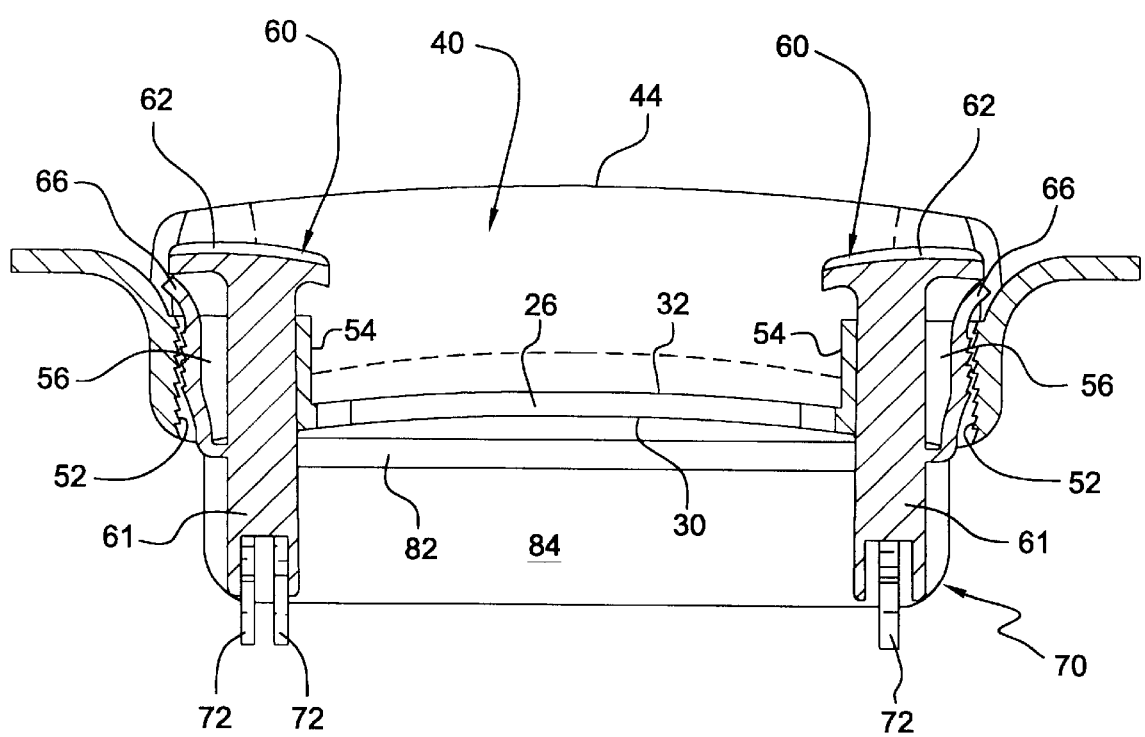
FIG. 10 is a cross sectional view taken along line 10—10 of FIG. 9.

The actuator 60 also includes a locking pawl 66 carried on its outer surface. This locking pawl is designed to engage with a mating ratchet fitting carried by the base 54 of the manually graspable tab 50. As best seen in FIGS. 5 and 10, the locking pawl 66 is provided with teeth on its outer face and these teeth are positioned to engage the teeth on the inner surface 52 of the base of the tab 50. This effectively provides mating ratchet fittings on the actuator and the manually graspable tabs to limit movement of the flanges back toward their insertion positions when the operator releases the actuator. In the absence of some arrangement to limit upward movement of the actuator, the tissue retracted by the flanges would tend to urge the flanges back toward one another, closing the opening and the tissue defined by the flanges.

The locking pawl 66 is desirably resiliently attached to the body 61 of the actuator. At some point, it may be necessary to remove the surgical access device 10 from the patient's body. To do so, one can urge the locking pawls 66 inwardly away from the inner surface 52 of the associated tab 50. Doing so will disengage the teeth of the pawl from the teeth of the tab, permitting the actuator to be withdrawn upwardly.

As noted above, FIG. 13 illustrates a slightly modified surgical access device 10'. The primary difference between this surgical access device 10' and the device 10 shown in FIGS. 1–10 is the inclusion of the recessed tracks 55' on the manually graspable tab 50 and the rails 63' on the actuator 60', as detailed above. However, FIG. 13 also shows an insert 200 which is useful in extending the utility of the invention. While this insert 200 is only shown used in connection with the surgical access device 10' of FIG. 13, the same insert 200 could easily be used with the embodiment illustrated in FIGS. 1–10.

Figure 13:
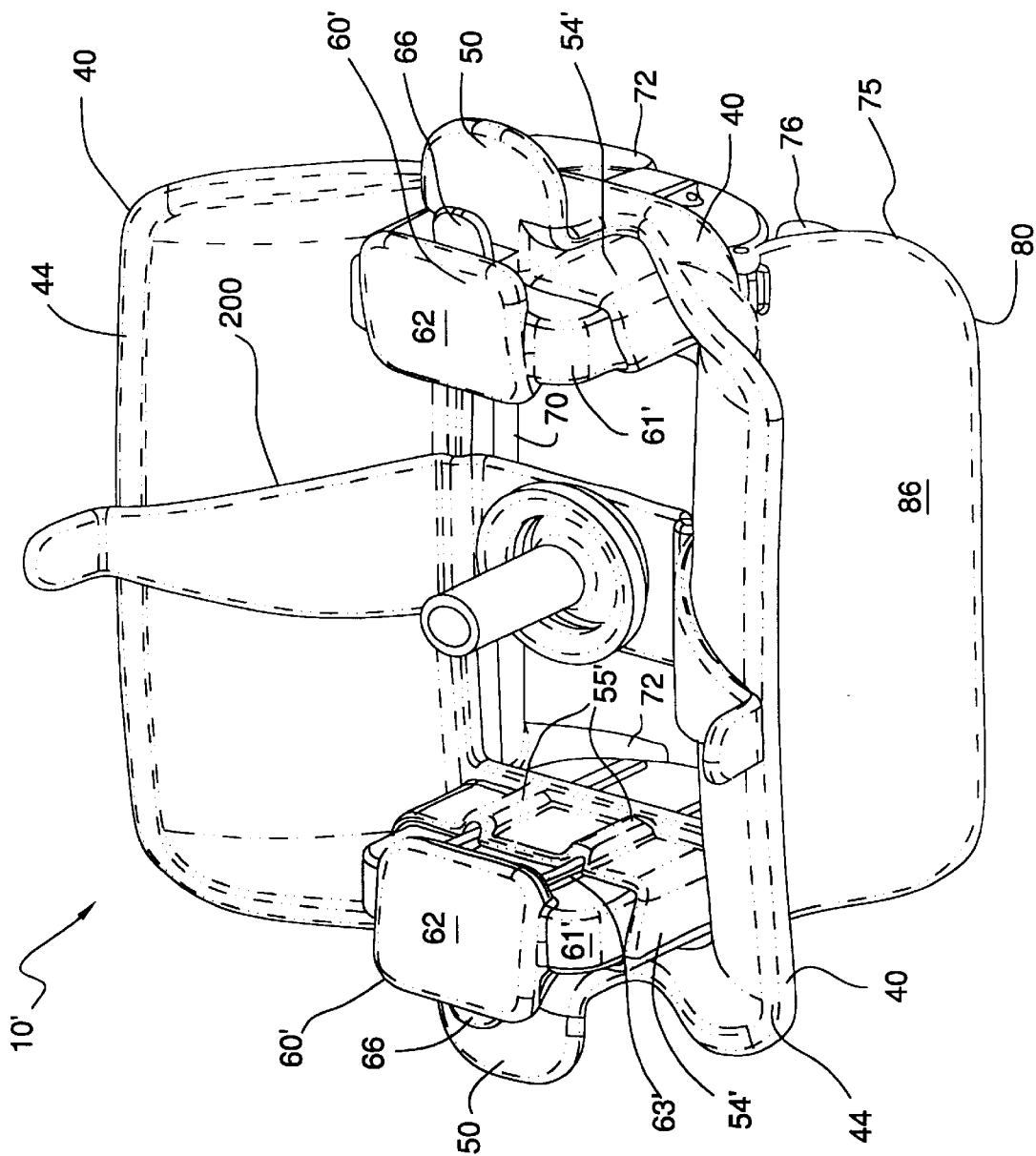
FIG. 13 is a top perspective view of a surgical access device in accordance with an alternative embodiment of the invention, the surgical access port also including a removable insert.
Figure 14:
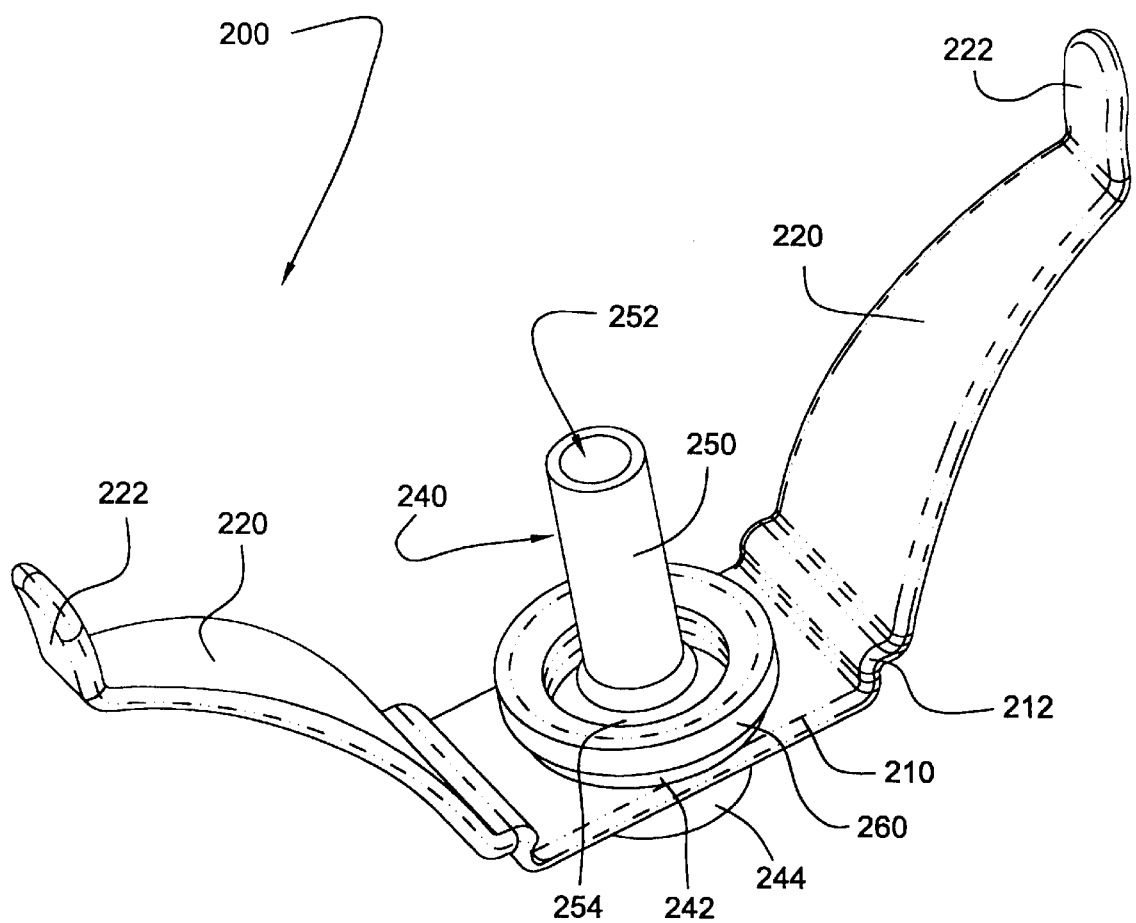
FIG. 14 is a top perspective view of the insert of FIG. 13.
Figure 15:
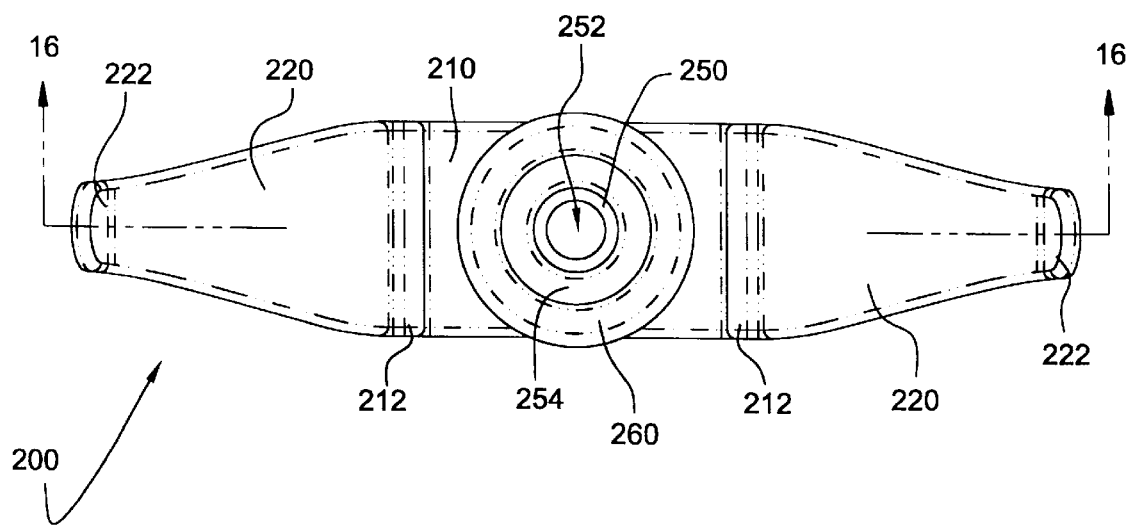
FIG. 15 is a top view of the insert of FIG. 14.
Figure 16:
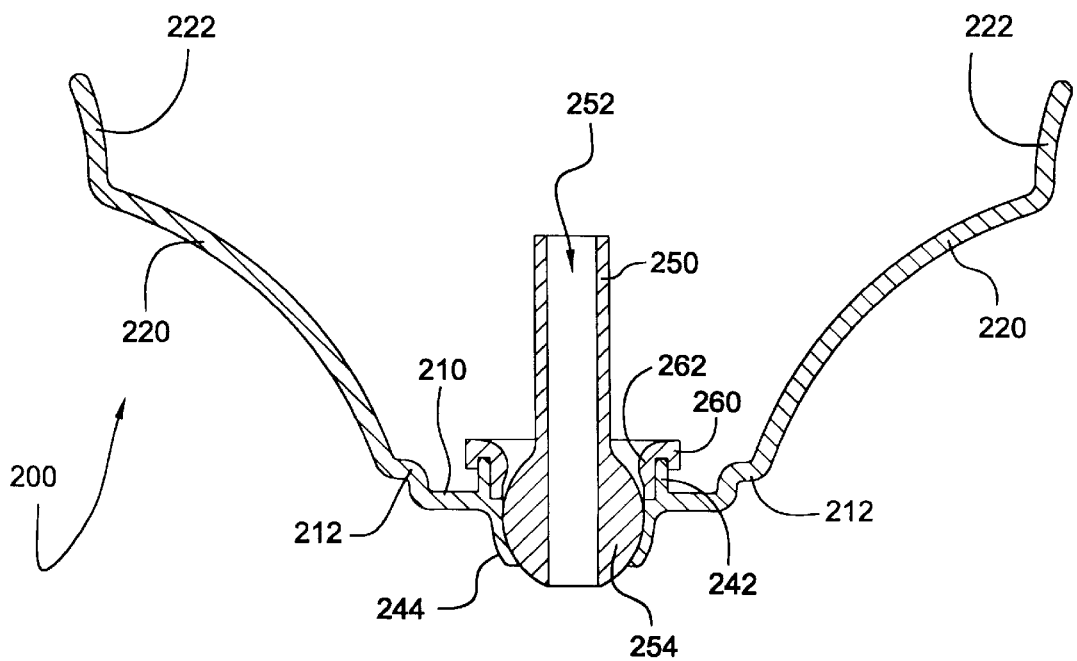
FIG. 16 is a schematic cross sectional view taken along line 16—16 of FIG. 15.

FIG. 13 illustrates the insert 200 in place on the surgical access device 10' while FIGS. 14–16 provide more detailed isolational views of the insert 200. The insert 200 generally includes a base 210 with a pair of upstanding wings 220 extending upwardly from either end of the base. The base 210 is sized to be received within the access port 22 of the frame 20 of the surgical access device. In a preferred embodiment, the junction between the base 210 and each wing 220 includes a step 212. This step 212 can rest on the upper surface of the frame 20 adjacent one of the longitudinal sides 26, 27 of the access port. While the fit of the base within the access port can be fairly snug, in a preferred embodiment it is a relatively loose fit, permitting the insert 200 to slide longitudinally along the length of the access port if the need arises.

The wings 220 of the insert are adapted to rest on the upper surface of the wings 40 of the flange 20 of the surgical access device. If so desired, the upper ends of these wings 220 of the insert can be provided with upwardly extending tabs 222. These tabs allow an operator to lift the insert 200 off of the frame 20 when it is no longer needed.

Figure 17:
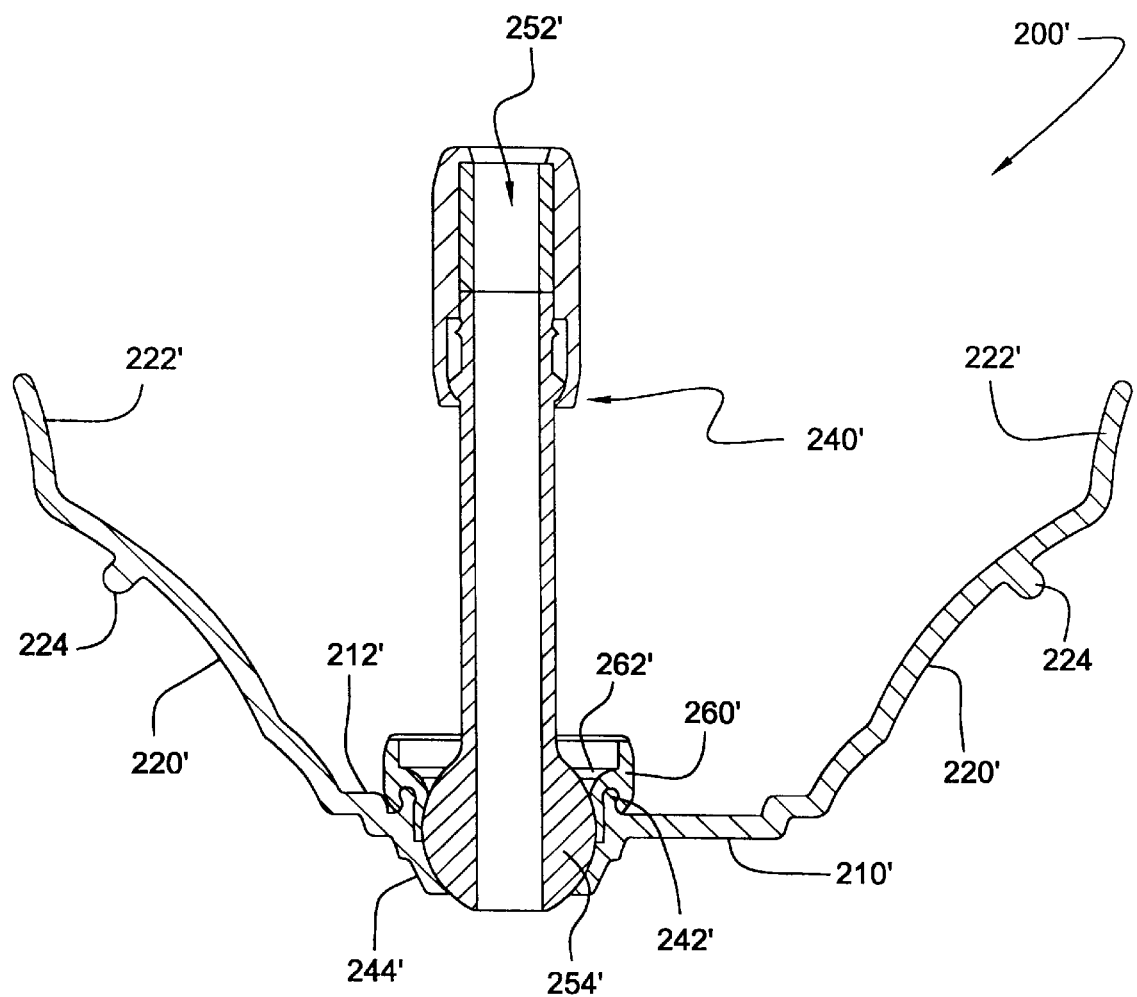
FIG. 17 is a schematic cross sectional view similar to FIG. 16, but illustrating an insert in accordance with another embodiment of the invention.

If so desired, the insert and the frame can be provided with mating fittings to more securely fasten the insert to the frame and to limit movement of the insert with respect to the frame once it is in place. FIG. 17 illustrates an alternative insert 200' which includes such a fitting. In particular, the lower surface of at least one of the wings 220' of the insert can be provided with a peg 224. This peg 224 can be received in through-holes (not shown) which pass through the wings 40.

The peg is desirably oriented generally laterally outwardly rather than downwardly. Optimally, there is a plurality of through holes in the wings, with the through-holes being arranged as spaced-apart pairs of holes, with one hole of each pair being positioned on each wing at a location laterally opposite the other hole of the pair. This will permit an operator to disengage the pegs 224 from the through-holes in the wings simply by urging the tabs 222' at the tops of the wings toward one another and slide the base longitudinally across the access port 22. Once the insert 200' is positioned where desired, the pegs can be seated in a new pair of through-holes in the wings.

The primary purpose of the insert 200 illustrated in FIGS. 13–16 is to provide an articulatable fitting 240. This fitting may be adapted to support a surgical implement at a desired position with respect to the frame. The fitting 240 can generally comprise a threaded collar 242 (best seen in FIG. 16) extending upwardly from the top of the base 210. A lower seat 244 can extend downwardly from the lower face of the base. The seat 244 desirably tapers radially inwardly downwardly away from the base.

In the embodiment of FIGS. 13–16, the fitting 240 is generally centered on the base 210. In the insert 200' of FIGS. 17 and 18, however, the fitting 240' is positioned closer to one of the two wings 220' than to the other. As shown in FIG. 18, this offset design allows one to position several inserts 200' adjacent one another on the frame 20 with the positions of the fittings 240' staggered from one insert to the next. Staggering the fittings in this fashion will minimize interference of the medical devices mounted in the fittings with one another. The use of multiple inserts in this fashion also highlights the versatility of the illustrated embodiments of the invention. At different stages of the procedure, a physician may want unfettered access to the entire width of the access port while at other stages, it may be more desirable to have the device hold one or more implements to free the physician's hands for other tasks. By adding or removing these inserts 200 or 200', the physician can vary the open surface of the access port from being fully open, to being partially open but partially covered one or more inserts, to being completely covered with a series of inserts.

The articulatable fitting 240 also includes a support tube 250. This support tube has a lumen 252 through which a suitable surgical device (e.g., an endoscope) can be inserted and maneuvered. The tube 250 also includes a hemispherical lower portion 254 which is supported in the lower seat 244, as best seen in FIG. 16. The hemispherical lower portion can be retained adjacent the lower seat 244 by a cap 260. This cap is desirably threaded to engage the threaded collar 242 of the base. The cap also includes an inwardly extending lip 262 to define an inner diameter which is smaller than the maximum outer diameter of the hemispherical lower portion 254 of the support tube, keeping the support tube in place.

This articulatable fitting allows a physician to pass a surgical implement through the lumen 252 of the support tube 250. By moving the support tube with respect to the base 210, the physician can readily maneuver any surgical implement into a different orientation with respect to the patient's internal cavity. If so desired, one can replace the illustrated fitting 240 with any appropriate articulatable fitting known in the art, e.g., those disclosed in the following U.S. Patents (the teachings of each of which are incorporated herein by reference): U.S. Pat. Nos. 5,375,588 (Yoon), 5,682,272 (Hasson), 3,021,842 (Flood), 3,017,887, (Heyer) and 3,016,899 (Stenwall).

Since the surgical access device 10 or 10' will be in direct contact with the patient's tissue, it should be formed of a biocompatible material. The specific material chosen will depend on a number of factors, including the anticipated mechanical stresses on the parts during use, whether it will be discarded after a single use or, less likely, will be sterilized and reused on different patients, etc. In order to minimize manufacturing costs if the devices are intended to be disposable, all of the parts can optimally be formed of an injection moldable plastic material, such as a biocompatible organic resin or thermoplastic material. Given the present teaching, the selection of an appropriate material for a given clinical application should be well within the capabilities of a skilled designer.

As noted above, the present invention also contemplates a method of gaining surgical access to a body cavity. In the following discussion, reference is made to the embodiments of the invention illustrated in FIGS. 1–10. It is to be understood, however, that these figures are used solely for convenience and that the present method can be utilized with devices which differ significantly from the embodiments illustrated in the drawings so long as they serve the functions called for in the method.

In accordance with this method, the operator is presented with a surgical implant, e.g., the surgical access device 10 illustrated in FIGS. 1–10. The physician cuts an elongate, generally linear incision through the patient's tissue. This incision should be at least as long as the leading edge E of the surgical access device 10. If so desired, one can minimize the length of this incision to be substantially the same as the length of the leading edge E of the device 10. It would be advisable to make such an incision generally I-shaped, however, with a pair of shorter transverse incisions at each end of the longer main incision. This will define a pair of tissue flaps which can be spread apart by the flanges 70, 75. If such short transverse incisions are not made, the physician would risk tearing the tissue when the flanges are moved from their insertion position to a retraction position.

The incision can pass through the entire thickness of the patient's tissue, including both cutaneous and subcutaneous layers. In one preferred method, though, the physician will first separate the cutaneous tissue from the subcutaneous tissue. The cutaneous tissue can be pulled back, and the incision can be made in the exposed subcutaneous tissue.

This is particularly desirable when one is using the surgical access device 10 to gain access to the patient's thoracic cavity through the intercostal space between adjacent ribs.

Once a suitable incision has been made through the patient's tissue, the leading edge E of the surgical access device 10 can be inserted into the incision. The surgeon will typically urge a length of each of the first and second flanges through the incision by pushing downwardly on the frame 20. Preferably, the flanges are inserted far enough through the incision to position the leading edges 80 of the flanges below the inner surface of the tissue, i.e., the tissue surface which faces the body cavity.

Once the flanges 70, 75 have been properly inserted into and extend through the incision, the physician can urge the flanges laterally away from one another. In the illustrated embodiment of the surgical access device, the physician need only move the actuators 60 downwardly within the actuator channels 56 of the manually graspable tabs 50. This can be facilitated by placing one finger of each hand beneath the manually graspable tab at either end of the frame 20. The operator can then press down on the actuator 60 by pushing the pad 62 of the actuator with a thumb, using the manually graspable tab to provide leverage.

As the actuators 60 are pushed down and urge the flanges away from one another, the flanges will expand the opening through the patient's tissue initially defined by the incision. Since the actuators will deploy the flanges at the same rate, the device inherently tends to center the access port laterally within the expanded opening.

As noted above, the leading edges 80 of the flanges are desirably positioned below the inner surface of the tissue. When the flanges are moved from their insertion position (FIGS. 1–5) laterally away from one another toward a retracting position, the leading edges of the flanges will tend to grasp the lower surface of the tissue. Once the incision has been widened enough to permit any reasonable access, the flanges have reached a first retracting position and the operator may simply stop. Desirably, the mating ratchet fittings on the actuator 60 and manually graspable tab 50 are designed to engage one another to lock the flange in such a position.

More preferably, though, the operator will not stop at the first narrow opening but instead continues to move the flanges through a wider range of retracting positions until the frame is suitably seated in the tissue. When the operator continues to move the flanges 70, 75 away from one another, the outer surfaces 86 of the flanges will act upwardly against the lower surface of the tissue with increasing force. This will draw the frame downwardly with respect to the tissue, helping seat the frame in the tissue. Desirably, the operator will continue urging the flanges away from one another until the access port 22 is positioned below the upper surface of the tissue in which the incision was initially made. In this position, the tissue is retained between the outer surface 86 of each flange and the concave outer surface 42 of the adjacent wing 40. This will rather securely position the access port 22, enabling an operator to reliably move medical instruments through the access port into the body cavity without fear of inadvertently moving or dislodging the surgical access device 10.

There are numerous advantages to the present invention over prior art retractors or access ports. Among these advantages are the self-seating characteristics of the surgical access device 10 and the improved accessibility of the body cavity attained in this fashion.

Prior art retractors simply provide a means for spreading the margins of an incision away from one another. Such retractors typically cannot engage the tissue and hold themselves in place. As a result, the physician must rely on friction between the tissue and the retractor to keep the retractor in place. The surgical access device 10 of the present invention, however, provides a much more secure connection between the retractor and the tissue being retracted.

The wings 40 of the access device perform a couple of functions which significantly enhance the physician's easy access to the body cavity through the access port 22. First, the tissue is retained between the flanges 70, 75 and the adjacent wings 40, helping seat the device in the desired position. The wings will also tend to keep both the subcutaneous tissue and any loose cutaneous tissue away from the open access port 22. In a preferred embodiment, the wings desirably extend at least about 10 mm above the upper surface of the access port 22. If so desired, the upper edge 44 of each of the wings can extend further upwardly or be specifically shaped to better retain the cutaneous tissue away from the opening.

The surgical access device 10 also provides superior access to the bodily cavity. This is attributable, at least in part, to the action of the flanges against the under side of the tissue. First, pulling the access port 22 downwardly toward the bottom of the tissue will increase the physician's range of motion laterally within the body cavity. In addition, the flanges will help lift the tissue upwardly on either side of the access port. This will also enhance the ability of the physician to gain access to structures positioned laterally with respect to the site of the incision. This is in direct contrast to devices such as the surgical cannula proposed by Garrison et al. in U.S. Pat. No. 5,613,937, discussed above. This long surgical cannula significantly restricts the range of angles through which the medical devices passed through the cannula can be maneuvered.

The physician can remove the surgical access device 10 by retracting the locking pawls 66 of each of the actuators. The physician can then raise the actuators upwardly, permitting the flanges to move back toward their insertion position (FIGS. 1–5). This will permit the surgical access device 10 to be removed from the patient and the tissue can simply be stitched back together.

It is envisioned, however, that in some circumstances a physician may want to gain access to the same bodily cavity later. For example, when conducting a lobectomy, a physician may need to gain access to the same lung to remove more of the lung tissue to ensure a safe margin around a tumor which is being removed. In such a circumstance, it may be desirable to leave the surgical access device 10 in place for an extended period of time.

If the physician does desire to retain the surgical access device 10 in place in the patient's tissue, the access port 22 should be sealed to prevent any infection. This can be accomplished in a wide variety of fashions. If the cutaneous tissue was pulled back and the surgical access device is seated in the subcutaneous tissue, the physician can bring the cutaneous tissue over the upper surface of the frame and suture that cutaneous tissue closed over the frame. The physician can then simply cut through the cutaneous tissue again and have unrestricted access to the same site in the bodily cavity.

For longer-term implantation, it may be desirable to more effectively seal the access port 22. In one embodiment of the invention, the access port 22 is closed by means of an insert (not shown in the drawings) sized to cover the entire access port 22. Such an insert would typically have a flat base without any openings therein and the insert could be snapped into place to seat this flat plate within the access port, effectively sealing it. The physician may want to place gauze or some other material on the upper surface of this insert to help keep it in place before suturing the cutaneous tissue over the surgical access device.

The bulk of the device 10 or 10' may be too large to be comfortably retained under the patient's skin as a longer-term implant. The ability of the device to seat itself downwardly in the incision will help, but a physician may prefer to remove the device 10' prior to closing the cutaneous tissue. Even if the physician would like to access the same site, leaving the opening in the subcutaneous tissue open may unnecessarily increase the risk of infection.

In accordance with a further method of the invention, the physician may employ a resilient membrane (not shown) to help seal the opening in the subcutaneous tissue after the surgical access device 10 or 10' has been removed from the opening. The membrane may comprise a disk-shaped mat of a resilient material having a reinforcing ring around its outer periphery. In use, the physician can place the membrane on top of the tissue through which the incision is to be made. If so desired, the membrane may be anchored in place by suturing the reinforcing ring to the tissue or by means of a biocompatible, sterile contact adhesive or the like.

Once the membrane is positioned, the physician can cut the incision through the patient's tissue. If so desired, the membrane can be provided with a pre-formed, self-closing gate therethrough and the physician can simply cut the patient's tissue by passing the scalpel through this gate. Alternatively, the membrane can be solid and the physician can cut through both the membrane and the patient's tissue when making the incision. The surgical access device 10 or 10' can then be deployed in the same fashion as outlined above, with the flanges being inserted through both the membrane and the patient's tissue.

After the procedure is complete, the physician can remove the surgical access device 10 or 10' from the opening, leaving the resilient membrane in place over the patient's tissue. The central part of the resilient membrane surrounding the incision should be formed of a material which is capable of resiliently closing the opening therein. Removing the implant will allow the opposed cut surfaces of the patient's tissue to move toward one another so cut edges (or the edges of the pre-formed gate, if such a gate is used) of the resilient membrane may abut one another. This abutment desirably generally seals the opening in the membrane and the physician may then suture the cutaneous tissue over the incision. To further enhance the seal of the membrane, the physician can suture the membrane shut or can use a biocompatible cementing compound to help seal the membrane before the cutaneous tissue is sutured over the membrane. (Both absorbable and nonabsorbable cements are known in the art.)

The central part of the membrane which will help close the opening can be formed of any suitable material. For example, it may comprise a relatively thick sheet of a relatively soft elastomeric material, with the abutting edges of the soft sheet to seal the opening, i.e., to serve as a barrier which will significantly limit the passage of bodily fluids or, perhaps, even bacteria, therethrough. Alternatively, it may comprise a bat of a resilient fibrous material enclosed in a resilient elastomeric shell. When the cut edges of the membrane abut one another again, the fibers of the bat can help seal the opening. If the membrane includes a reinforcing ring, the ring can be integrally formed with the rest of the membrane or it can be formed as a separate component and later attached to the rest of the device.

While a preferred embodiment of the present invention has been described, it should be understood that various changes, adaptations and modifications may be made therein without departing from the spirit of the invention and the scope of the appended claims.

What is claimed is:

1. A surgical device for accessing a body cavity, comprising:
   a) a frame defining an access port, the frame having a lower surface;
   b) a first flange having an elongate leading edge, the first flange being carried on the lower surface of the frame adjacent a first side of the access port and being pivotable between an insertion position and at least one retracting position; and
   c) a second flange having an elongate leading edge, the second flange being carried on the lower surface of the frame adjacent a second side of the access port, the first and second sides of the access port being opposite one another, and being pivotable between an insertion position and at least one retracting position; the first and second flanges each being shaped so that when the first and second flanges are both in their insertion position, their leading edges are positioned immediately adjacent one another and together define an elongate, generally linear leading edge of the device which can be inserted into a single, elongate incision, the leading edge of the device being positioned below the access port.

2. The surgical device of claim 1 wherein the first flange is attached to the lower surface of the frame by a first hinge and the second flange is attached to the lower surface of the frame by a second hinge, the first and second hinges being parallel to one another and extending generally longitudinally along the lower surface of the frame.

3. The surgical device of claim 2 wherein the first and second hinges define spaced-apart first and second pivot axes about which the first and second flanges, respectively, pivot, the pivot axes together defining a plane which is generally perpendicular to the direction in which the leading edge is inserted into said incision.

4. The surgical device of claim 1 wherein each of the flanges has a convex inner face which is oriented toward the access port when the flange is in its insertion position.

5. The surgical device of claim 4 wherein each flange has a concave outer face adapted to face tissue and retain the tissue between the flange and the lower surface of the frame.

6. The surgical device of claim 1 wherein the frame has a pair of wings, one wing extending upwardly at an angle from a position adjacent each of the first and second sides of the access port.

7. The surgical device of claim 6 wherein each wing has a concave lower surface, permitting a central portion of the frame to seat within said incision at a level below the upper surface of surrounding tissue when each of the flanges is in a retracting position.

8. The surgical device of claim 1 further comprising at least one actuator adapted to engage a deployment surface of each of the first and second flanges to permit an operator to urge the flanges from their respective insertion positions to respective retracting positions.

9. The surgical device of claim 1 wherein the access port has opposed first and second ends, further comprising a first actuator carried by the frame at the first end of the access port and a second actuator carried by the frame at the second end of the access port, each of the actuators having a control surface adapted to engage a deployment surface of each of the first and second flanges to permit an operator to urge the flanges from their respective insertion positions to respective retracting positions.

10. The surgical device of claim 9 further comprising first and second manually graspable tabs carried by the frame adjacent the first and second ends of the access port, respectively, each of the first and second tabs carrying a ratchet fitting adapted to engage a mating ratchet fitting on an associated actuator to limit movement of the flanges toward their insertion positions when an operator lets go of the actuator.

11. The surgical device of claim 1 further comprising at least one insert releasably attached to the frame, the insert being releasably retained in and extending through the access port.

12. A surgical device for accessing a body cavity, comprising:
   a) a frame defining an access port and having a lower surface, the frame having a pair of laterally extending wings having a concave lower surface extending generally upwardly away from opposed first and second longitudinal sides of the access port;
   b) a first flange carried on the lower surface of the frame adjacent the first side of the access port and being pivotable between an insertion position and at least one retracting position;
   c) a second flange carried on the lower surface of the frame adjacent the second side of the access port and being pivotable between an insertion position and at least one retracting position; the first and second flanges in their retracting positions being adapted to urge upwardly against an internal surface of a patient's tissue to seat the access port below the tissue's upper surface.

13. The surgical device of claim 12 wherein each of the first and second flanges has a concave outer face adapted to face the internal surface of the tissue and retain the tissue between the flange and the lower surface of the adjacent wing.

14. The surgical device of claim 12 wherein each of the wings extend upwardly at least about 10 mm above the access port, thereby permitting the wings to effectively retain cutaneous tissue away from the access port when the access port is seated below an upper surface of subcutaneous tissue.

15. The surgical device of claim 12 wherein the access port has opposed first and second lateral ends, further comprising a first actuator carried by the frame at the first end of the access port and a second actuator carried by the frame at the second end of the access port, each of the actuators having a control surface adapted to engage a deployment surface of each of the first and second flanges to permit an operator to urge the flanges from their respective insertion positions to respective retracting positions.

16. A method of gaining surgical access to a body cavity, comprising:

a) providing a surgical implant comprising a frame defining an access port; a first flange carried on a lower surface of the frame and having an elongate leading edge; and a second flange carried on the lower surface of the frame and having an elongate leading edge, the second flange being adjacent a side of the access port opposite the first flange; the leading edges of the first and second flanges being positioned immediately adjacent one another to together define an elongate, generally linear leading edge of the implant;

b) making an elongate, generally linear incision through the patient's tissue, the incision being at least as long as leading edge of the implant and defining an opening through the patient's tissue;

c) inserting the leading edge of the implant into the incision and urging a length of each of the first and second flanges through the incision;

d) urging the first and second flanges laterally away from one another, thereby simultaneously expanding the opening through the patient's tissue and centering the access port laterally within the opening.

17. The method of claim 16 wherein each of the flanges have a concave outer face adapted to face the tissue, the method further comprising retaining a portion of the tissue between each of the flanges and the lower surface of the frame.

18. The method of claim 16 wherein the flanges are inserted far enough through the incision to position their leading edges below an inner surface of the tissue which faces the body cavity.

19. The method of claim 18 wherein the lower surface of the frame extends generally upwardly and laterally outwardly away from the access port, the first and second flanges being urged a sufficient distance laterally away from one another to seat the access port below the tissue's upper surface.

20. The method of claim 16 wherein the elongate, generally linear incision is made in subcutaneous tissue, the method further comprising bringing cutaneous tissue over an upper surface of the frame and suturing the cutaneous tissue closed over the frame.

21. The method of claim 20 further comprising the steps of:
   a) providing a resilient membrane;
   b) prior to the insertion of the leading edge of the implant into the incision through the tissue, positioning at least a portion of the resilient membrane over the patient's tissue surrounding the incision site; and
   c) withdrawing the implant from the opening, leaving the resilient membrane in place over the patient's tissue.

22. The method of claim 21 wherein the resilient membrane is positioned over the patient's tissue prior to making the incision in the patient's tissue, withdrawal of the implant from the opening permitting opposed cut surfaces of the tissue to move toward one another so cut edges of the resilient membrane will abut one another.

* * * * *